US012691193B2

(12) United States Patent
Kim et al.

(10) Patent No.: US 12,691,193 B2
(45) Date of Patent: Jul. 28, 2026

(54) STERILISATION OF ENDOSCOPES

(71) Applicant: University of Southampton, Southampton (GB)

(72) Inventors: Min Kwan Kim, Southampton (GB); Charles William Keevil, Southampton (GB); Rodolphe Christian Hervé, Southampton (GB); Henrike Jakob, Southampton (GB)

(73) Assignee: University of Southampton, Southampton (GB)

( * ) Notice: Subject to any disclaimer, the term of this patent is extended or adjusted under 35 U.S.C. 154(b) by 742 days.

(21) Appl. No.: 17/926,699

(22) PCT Filed: May 27, 2021

(86) PCT No.: PCT/EP2021/064267
§ 371 (c)(1),
(2) Date: Nov. 21, 2022

(87) PCT Pub. No.: WO2021/239909
PCT Pub. Date: Dec. 2, 2021

(65) Prior Publication Data
US 2023/0201390 A1 Jun. 29, 2023

(30) Foreign Application Priority Data

May 29, 2020 (GB) .................................... 2008127

(51) Int. Cl.
| | |
|---|---|
| *A61L 2/14* | (2006.01) |
| *H05H 1/24* | (2006.01) |
| *A61L 103/15* | (2026.01) |

(52) U.S. Cl.
CPC ............. *A61L 2/14* (2013.01); *H05H 1/2418* (2021.05); *H05H 1/2425* (2021.05);
(Continued)

(58) Field of Classification Search
CPC ....................................................... A61L 2/14
See application file for complete search history.

(56) References Cited

U.S. PATENT DOCUMENTS

| | | | |
|---|---|---|---|
| 8,647,585 B2 | 2/2014 | Hancock | |
| 2005/0121607 A1* | 6/2005 | Miller ................. | H05H 1/2406 |
| | | | 250/288 |

(Continued)

FOREIGN PATENT DOCUMENTS

| | | | |
|---|---|---|---|
| CN | 206761952 U | | 12/2017 |
| JP | 2008034184 A | * | 2/2008 |

(Continued)

OTHER PUBLICATIONS

English Translation of Japanese Document Identification No. JP 2008034184 A directed to Masaaki provided by the United States Patent and Trademark Office Search Tool SEARCH: Nagatsu Masaaki; Generation Method and Generation Device of Thin Line-Like Atmospheric Discharge Plasma; Feb. 14, 2008 (Year: 2008).*

(Continued)

*Primary Examiner* — Kevin Joyner
(74) *Attorney, Agent, or Firm* — POLSINELLI PC

(57) ABSTRACT

A flexible elongate atmospheric plasma generator for generating a transverse atmospheric plasma within configured for insertion into an internal channel of an elongate endoscope tube, the plasma generator including an elongate body of dielectric material, an elongate first electrode centrally located within the body of dielectric material and an elongate second electrode around an elongate external surface of the body of dielectric material, the second electrode having a plurality of electrically conductive elements forming a mesh defining holes in the second electrode, wherein application of a potential difference across the first and second
(Continued)

electrodes can generate a plasma within atmospheric air surrounding the atmospheric plasma generator.

32 Claims, 8 Drawing Sheets

(52) U.S. Cl.
CPC ........ *H05H 1/2431* (2021.05); *A61L 2103/15* (2026.01); *H05H 2245/36* (2021.05)

(56) References Cited

U.S. PATENT DOCUMENTS

| | | | |
|---|---|---|---|
| 2012/0046597 A1* | 2/2012 | Morfill | H05H 1/2406 |
| | | | 604/20 |
| 2015/0340207 A1 | 11/2015 | Holbeche | |
| 2016/0113700 A1 | 4/2016 | Hancock et al. | |

FOREIGN PATENT DOCUMENTS

| | | | |
|---|---|---|---|
| WO | 2011/091842 | A1 | 8/2011 |
| WO | 2019/130223 | A1 | 7/2019 |
| WO | 2019/175063 | A1 | 9/2019 |
| WO | 2020/123679 | A1 | 6/2020 |

OTHER PUBLICATIONS

International Preliminary Report on Patentability in related international application No. PCT/EP2021/064267 issued on Nov. 17, 2022.

Search Report Under Section 17(5) in related GB application No. 2008127.9 issued on Nov. 25, 2020.

International Search Report and Written Opinion in related international application No. PCT/EP2021/064267 issued on Sep. 20, 2021.

* cited by examiner

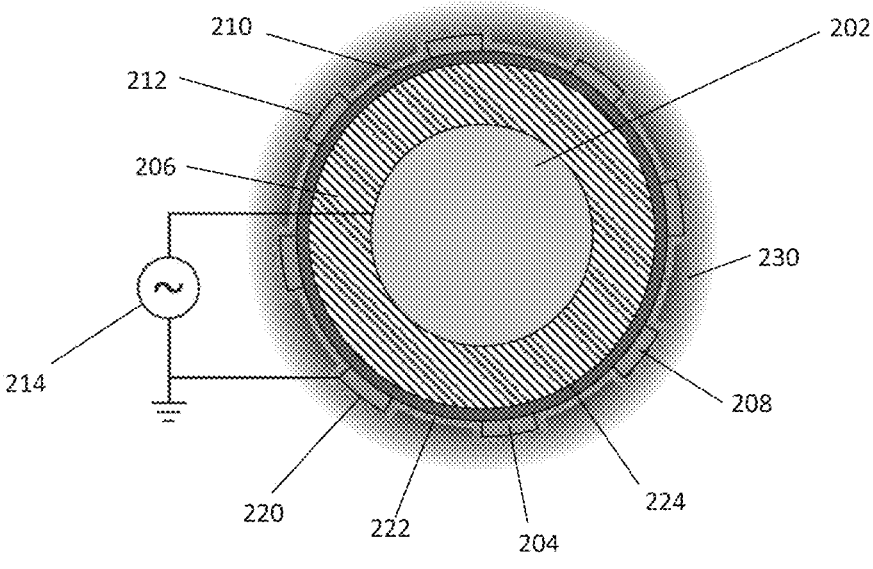
FIG. 9
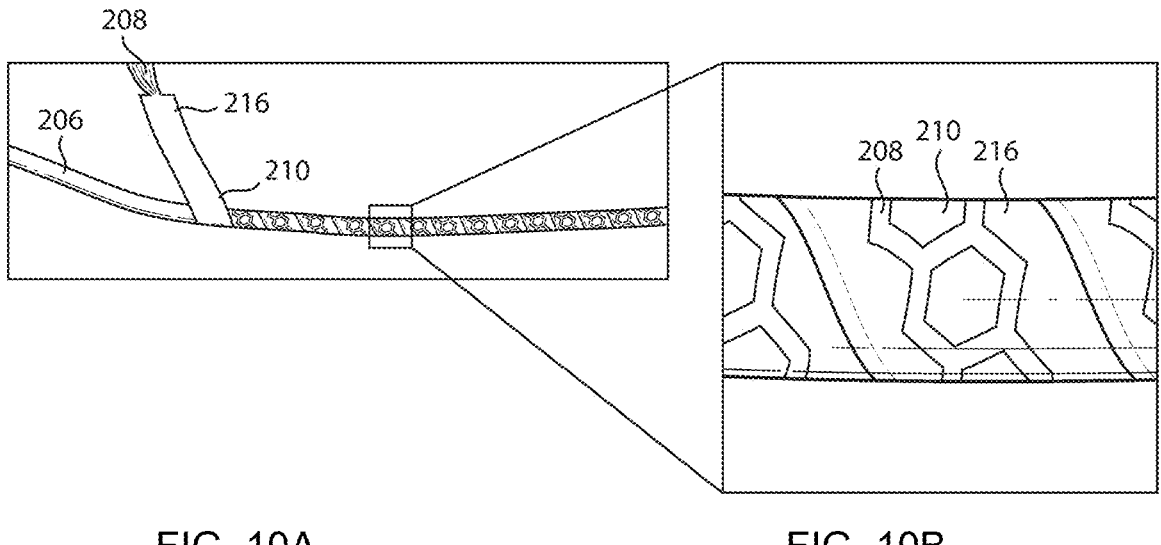
FIG. 10A                              FIG. 10B

STERILISATION OF ENDOSCOPES

FIELD OF THE INVENTION

The present invention relates to an apparatus for, and a method of, sterilising endoscopes.

BACKGROUND

Flexible endoscopy is a widely used diagnostic and therapeutic procedure. As flexible endoscopes may become heavily contaminated with blood, secretions, and microorganisms during use, there have been sporadic reports of nosocomial infections linked to endoscopic procedures. Current reprocessing of flexible endoscopes involves cleaning and high-level disinfection followed by rinsing and drying before storage. Most contemporary flexible endoscopes cannot be heat sterilized and are designed with narrow lumens and multiple internal channels, which makes them difficult to clean and disinfect appropriately. If these instruments are not properly cleaned, the disinfection and drying procedures can fail and increase the possibility of transmission of infection from one patient to another.

Residual contamination in endoscope channels is a global, emerging problem due to the increased demand for endoscopic interventions beyond the original remit of first endoscopes (simple observation, when bacterial contamination was considered a minor problem) and the development of antimicrobial resistance in a range of pathogens. Factors such as high risk of infections associated with improper sterilization of endoscopes, increasing investments, funds, and grants by government bodies across the globe, rising number of hospitals and growing hospital investments in endoscopy instruments, and rising prevalence of diseases that require endoscopy procedures are driving the growth of the global market for endoscope reprocessing. A technology capable of overcoming the limitations of HLD (High-level disinfection) for flexible endoscopes would be welcome in endoscopy units worldwide.

As the material composition of most flexible endoscopes do not allow use of steam to sterilise their channels, the current reprocessing regimen for flexible luminal endoscopes relies on manual wash followed by automated chemical disinfection. This requires the immersion of the endoscope and its accessories in a cleaning solution for a minimum contact time at the appropriate temperature and concentration while the different channels are brushed to remove gross contamination. The endoscopes are then placed in an automated endoscope reprocessor for High Level Disinfection (HLD) which also relies on a chemical solution or gas being passed through the sealed channels to reduce the bacterial load, prior to a final rinse with water.

Evidence shows that even applied according to manufacturer's recommendations this protocol is not sufficient to kill all bacterial within the channels. Moreover, residues of chemical disinfectants may remain despite the final rinse and cause complications in patients, such as chemical colitis.

HLD relies on water-based or gas chemicals with limited efficacy against established biofilms and/or potentially serious health hazards for clinical staff. Chemicals should be used at the correct temperature, in combination with complex sterilization and cleaning processes, and thus need to be operated by skilled professionals. It has been known that chemicals used in endoscope reprocessing can cause adverse effects affecting the healthcare professionals such as skin toxicity. Moreover, some bacteria and prions are resistant to existing endoscope reprocessing chemicals, which hinder the growth of endoscope reprocessing market.

As an alternative approach, non-chemical reprocessing methods have been investigated including atmospheric plasma jet, plasma activated water and ultrasonic bubbles. It is well known that non-thermal plasma and ultrasonic bubbles can effectively sterilise without destroying chemical, biological, and mechanical properties of flexible endoscope channels. As the lifetime of ultrasonic bubbles is about 20 μs, it is impractical to maintain sufficient ultrasonic cleaning power throughout the entire endoscope channel which typically has an internal diameter of 2~3 mm and a length of 1.5 m.

A plasma j et also quickly decays at atmospheric pressure due to fast dissociative recombination process of molecules. Therefore, the length of the atmospheric plasma jet plume is difficult to reach more than a couple of tens of centimetres.

Atmospheric plasma relying to the generation of short-lived sub-atomic species and its use have been developed and studied for years, though the key limitation has always been about delivery to the target at an effective range.

It is well known that reactive species can initiate and catalyse peroxidation and oxidation processes, which can degrade biological contaminants and lead to the formation of hydroxyl (OH) radicals which can kill and/or inactivate pathogens by the Fenton reaction. Therefore, several studies had been performed previously on the use of plasmas for infection control. Although plasma can be used to reprocess endoscope channels, previously it is difficult to introduce plasmas into an endoscope channel due to its size and length. As a typical luminal endoscope channel has 2~3 mm internal diameter and 1.5 m length, conventional methods to generate plasmas are not suitable for this kind of application.

The following three publications have addressed the problem of sterilising or reprocessing an endoscope using a plasma.

S. Wang, Z. Y. Chen, X. H. Wang, D. Li, A. J. Yang, D. X. Liu, M. Z. Rong, H. L. Chen, and M. G. Kong, "Propagation characteristics of atmospheric-pressure He+O2 plasmas inside a simulated endoscope channel," *Journal of Applied Physics,* 118, 203301 (2015). This publication describes the generation of atmospheric plasmas inside a simulated endoscope channel using a series of active and ground electrodes. However, the actual endoscope channel has a metallic casing thus the proposed method cannot be applied to actual endoscope channels.

Jörn Winter, Thalita M. C. Nishime, Sven Glitsch, Heike Lühder, and Klaus-Dieter Weltmann, "On the development of a deployable cold plasma endoscope," *Contrib. Plasma Phys*, Vol 58, Issue 5, 2018. This publication describes plasma generation inside an endoscope tube by a narrow electrode winding on the outside of the tube. However, the outside of the endoscope is fully covered with stainless steel wire mesh and a spiral metal band.

Jörn Winter, Thalita M C Nishime, Robert Bansemer, Martina Balazinski, Kristian Wende, and Klaus-Dieter Weltmann, "Enhanced atmospheric pressure plasma jet setup for endoscopic applications," Journal of Physics D: Applied Physics, Vol 52, No 2, 2018. This publication describes the development of a plasma jet source for endoscopic application. Although the system has a small dimension, the system is difficult to make long enough to treat the entire endoscope. Moreover, the system generated a very small jet at the centre and requires a continuous gas feeding.

These three papers therefore all disclose technically unsatisfactory solutions to the problem of sterilising or reprocessing an endoscope using a plasma.

WO-A-20191/75063 discloses an apparatus for sterilizing surgical scoping devices such as endoscopes, gastroscopes, laparoscopes and the like. A probe tip comprises first and second electrodes respectively connected to inner and outer conductors of a coaxial cable. The second electrode encloses an internal volume of the probe tip, and the first electrode extends longitudinally within the internal volume. A gas conduit is in fluid communication with the internal volume, and supplies working gas from a gas supply. The first electrode and second electrode are configured to receive RF and/or microwave energy from the coaxial cable to set up an electric field in the internal volume for striking a plasma therein. The probe tip includes an outlet for releasing plasma from the internal volume, so that the generated plasma flows out of the distal open end of the second electrode to contact an inner channel surface of the surgical scoping devices in which the probe tip is inserted.

CN-U-206761952, WO-A-2019/130223 and WO-A-2020/123679 disclose alternative apparatus and methods for sterilizing surgical scoping devices such as endoscopes using a plasma formed from a working gas supplied to the apparatus. In CN-U-206761952 and WO-A-2020/123679 a plasma is output from an outlet end of the apparatus into hollow channel of the endoscope, whereas in WO-A-2019/130223 no apparatus is inserted into the endoscope but a flow of plasma is passed through the hollow channel of the endoscope.

Outside the healthcare field concerned with the problem of reprocessing endoscopes, a paper by Heesoo Jung, Jin Ah Seo, and Seungki Choi, "Wearable Atmospheric Pressure Plasma Fabrics Produced by Knitting Flexible Wire Electrodes for the Decontamination of Chemical Warfare Agents", Scientific Reports, Vol 7, Article number 40746, 2017, discloses a fabric composed of knitted flexible wire electrodes which forms a large fabric surface for decontaminating chemical warfare agents.

Accordingly, there is a need in the healthcare art for a method, and an associated apparatus, for sterilising an interior surface of an elongate endoscope tube, which can reliably and repeatedly achieve a significantly higher degree of sterilisation than some known endoscope sterilisation techniques.

There is a further need in the healthcare art for a method, and an associated apparatus, for sterilising an interior surface of an elongate endoscope tube, which can avoid the use of cleaning solutions, and associated rinsing liquids, for cleaning the interior surface, and can also avoid the presence of residues of such cleaning solutions remaining on the interior surface after the cleaning and rinsing steps.

SUMMARY OF THE INVENTION

The present invention aims at least partially to overcome these problems, and meet these needs in the healthcare art.

The present invention aims to provide an improved apparatus and method to reduce healthcare-associated infections (HCAIs) by deactivating and removing bacterial biofilms and prions inside long, narrow, flexible luminal endoscope tubes.

Accordingly, in a first aspect the present invention provides an apparatus for sterilising an interior surface of an elongate endoscope tube by an atmospheric plasma, the apparatus comprising a flexible elongate atmospheric plasma generator for generating a transverse atmospheric plasma within, and along a length of, an elongate endoscope tube into which the atmospheric plasma generator has, in use, been inserted, the flexible elongate atmospheric plasma generator being configured for insertion into an end of, and along a length of, an internal channel of an elongate endoscope tube, the flexible elongate atmospheric plasma generator comprising an elongate body of dielectric material, an elongate first electrode centrally located within the body of dielectric material and an elongate second electrode around an elongate external surface of the body of dielectric material, wherein the second electrode comprises a plurality of electrically conductive elements forming a mesh defining holes in the second electrode, wherein the atmospheric plasma generator is configured such that application of a potential difference across the first and second electrodes can generate a plasma within atmospheric air surrounding the atmospheric plasma generator.

In a second aspect, the present invention provides a method of sterilising an interior surface of an elongate endoscope tube by an atmospheric plasma, the method comprising the steps of:

(a) providing an apparatus according to the present invention;

(b) inserting the flexible elongate atmospheric plasma generator into an elongate endoscope tube so that the elongate second electrode is in contact with atmospheric air within the elongate endoscope tube; and (c) supplying electrical power to the flexible elongate atmospheric plasma generator to cause the plasma generator to generate a transverse atmospheric plasma within the elongate endoscope tube.

The apparatus and method of the preferred embodiments of the present invention can generate a non-thermal transverse atmospheric plasma directly inside a luminal endoscope channel or bore, and the plasma can be generated along the whole length of the flexible elongate plasma generator, in the form, for example, of a flexible yarn, placed in an endoscope channel or bore. Consequently, an entire length of an endoscope tube can be simultaneously and quickly sterilised using the apparatus and method of the preferred embodiments of the present invention.

The preferred embodiments of the present invention can provide an accurate reprocessing system for flexible endoscope tubes.

The method of the preferred embodiments of the present invention can reprocess endoscope tubes by sterilisation within the interior of the endoscope tube using a transverse atmospheric plasma system (TAPS).

The apparatus of the preferred embodiments of the present invention can also provide a plasma generator of a transverse atmospheric plasma system (TAPS) which is self-cleaning, and optionally can additionally be cleaned using microscopic ultrasonic bubbles.

The apparatus and method of the preferred embodiments of the present invention can overcome the technical problems, disadvantages and barriers as described above of known endoscope sterilisation and reprocessing systems and methods. In particular, the apparatus and method of the preferred embodiments of the present invention can reliably and repeatedly achieve sterilisation and infection control of long, narrow, flexible endoscope tubes by generating non-thermal plasma directly inside the channels or bores of the endoscope tubes.

Consequently, the apparatus and method of the preferred embodiments of the present invention can provide a transverse atmospheric plasma system which can generate a homogenous thin plasma layer inside the whole length of endoscope channels or bores.

In the apparatus of the preferred embodiments of the present invention, a modular design is implemented for the flexible elongate atmospheric plasma generator, which functions as the plasma source during use, so that the length of the plasma source can be easily adjusted, and the electrode section can be replaced quickly if necessary.

After the sterilisation process using a transverse atmospheric plasmas system of the preferred embodiments, of the present invention, the surface of the flexible elongate atmospheric plasma generator can be contaminated by deactivated microorganisms and other residues. The method of the preferred embodiments can also carry out a self-cleaning process of the flexible elongate atmospheric plasma generator, optionally additionally using microscopic ultrasonic bubbles for cleaning away bulk or large debris, to enhance the reusability and microbiological safety of the plasma sterilising system.

The present inventors believe that the use of atmospheric plasma has never previously been applied successfully in the healthcare field for cleaning and sterilising the interior surfaces of endoscope tubes due to the limitations described above. The apparatus and method of the preferred embodiments of the present invention can provide a new plasma delivery technology which significantly and successfully addresses and solves the problem of residual biological contamination in long narrow lumens and endoscope tubes.

The apparatus and method of the preferred embodiments of the present invention can be applied on the reprocessing and infection control of endoscope channels, and thereby solve the problems associated with residual contamination in endoscope channels as discussed hereinabove. The apparatus and method of the preferred embodiments of the present invention can therefore provide a technology capable of overcoming the limitations of HLD (High-level disinfection) for flexible endoscopes.

The apparatus and method of the preferred embodiments of the present invention can produce non-thermal plasmas inside endoscope channels and bores and thus can use a plasma-induced Fenton reaction and advanced oxidation process during endoscope reprocessing.

Compared to the existing chemical-based reprocessing approach, the apparatus and method of the preferred embodiments of the present invention can provide an innovative reprocessing method, which does not use chemicals or heat. The chemical and physical characteristics of non-thermal plasmas can be easily adjusted and controlled by altering the power operating conditions such as frequency and operating voltage. The apparatus and method of the preferred embodiments of the present invention can, therefore, can be used to reprocess and disinfect various types of endoscopes without changing the apparatus.

The apparatus and method of the preferred embodiments of the present invention can be used to sterilise endoscope tubes against a range of relevant pathogens. The method of the preferred embodiments of the present invention has can be additive to existing sterilisation protocols. The method of the preferred embodiments of the present invention has the potential to replace HLD altogether, with the added benefit of reduced time, cost savings, reduced water consumption and reduced environmental impact.

BRIEF DESCRIPTION OF THE DRAWINGS

Embodiments of the present invention will now be described in more detail by way of example only with reference to the accompanying drawings, in which:

FIG. 9 is a transverse cross-section through a flexible elongate atmospheric plasma generator in accordance with a third embodiment of the apparatus of the present invention;

FIG. 10a is a perspective view of the flexible elongate atmospheric plasma generator illustrated in FIG. 9 during assembly of the flexible elongate atmospheric plasma generator;

FIG. 10b is an enlarged view of part of the flexible elongate atmospheric plasma generator illustrated in FIG. 10a;

Figure 1:
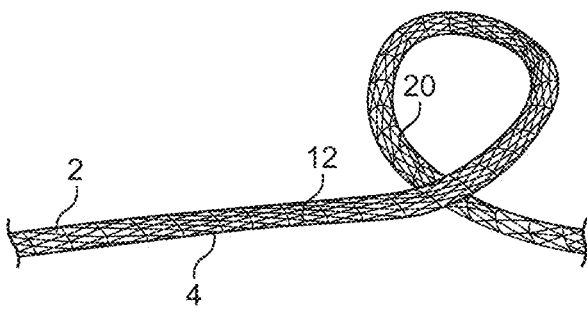
FIG. 1 is a perspective view of part of a length of a flexible elongate atmospheric plasma generator comprised in an apparatus for sterilising an interior surface of an elongate endoscope tube by an atmospheric plasma in accordance with a first embodiment of the apparatus of the present invention.
Figure 2:
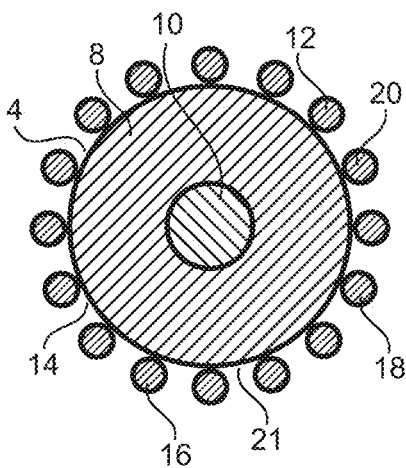
FIG. 2 is a transverse cross-section through the flexible elongate atmospheric plasma generator illustrated in FIG. 1.

It is to be noted that some of the drawings, other than photographs, are not to scale and some dimensions may be exaggerated for the purpose of clarity of illustration.

DETAILED DESCRIPTION

Referring to FIGS. 1 to 4, there is illustrated an apparatus for sterilising an interior surface of an elongate endoscope tube by an atmospheric plasma in accordance with a first embodiment of the present invention.

The apparatus 2 comprises a flexible elongate atmospheric plasma generator 4 for generating a transverse atmospheric plasma within, and along a length of, an elongate endoscope tube 6 into which the atmospheric plasma generator 4 has, in use, been inserted. Typically, the flexible elongate atmospheric plasma generator 4 is circular in transverse cross-section. In preferred embodiments, the flexible elongate atmospheric plasma generator 4 has an external diameter of from 1.5 to 5 mm, preferably from 2 to 5 mm, for example from 2 to 3 mm. Typically, and optionally in combination with any of these external diameter ranges, the flexible elongate atmospheric plasma generator 4 has a length of at least 50 cm, preferably from 1 to 3 metres, for example from 1 to 2 metres.

The plasma generator 4 comprises an elongate body 8 of dielectric material. Typically, the body 8 of dielectric material is composed of a flexible polymer, for example a silicone elastomeric material, or a flexible ceramic material. The body 8 of dielectric material is preferably circular in transverse cross-section and has an external diameter within the ranges of the external diameter of the plasma generator 4 as described above.

An elongate first electrode 10 is centrally located within the body 8 of dielectric material. Preferably, the first electrode 10 and the body 8 of dielectric material are coaxial. The first electrode 10 is typically composed of a flexible metal wire, typically comprising a plurality of wire filaments. Typically, the first electrode is circular in transverse cross section and has an external diameter of from 0.4 to 1 mm, optionally from 0.5 to 1 mm. Preferably, the first electrode 10 functions as the power electrode and the second electrode 12 functions as the ground electrode of the plasma generator 4. By providing that the outer electrode of the plasma generator 4 is grounded, the electrical safety of the plasma generator 4 is enhanced since an operator can safely contact the second electrode 12 even if the plasma generator 4 is electrically powered. As described hereinbelow, the plasma generator 4 also operates at a low electrical current which also enhances the electrical safety of the plasma generator 4 for the operator.

An elongate second electrode 12 is disposed around an elongate external surface 14 of the body 8 of dielectric material. The second electrode 12 comprises a plurality of electrically conductive elements 16 forming a mesh 20 defining holes 21 in the second electrode 12. The plurality of electrically conductive elements 16 forming a regular electrode array 18 surrounding the elongate external surface 14 of the body 8 of dielectric material. Typically, at least some of the elements 16 are oriented in a helical direction around the elongate external surface 14 of the body 8 of dielectric material. Typically, each element 16 has a width, measured in a circumferential direction around the plasma generator 4, or tangential to the circumferential direction, of from 0.1 to 0.5 mm, typically from 0.1 to 0.3 mm. In preferred embodiments of the present invention, in a transverse cross-section through the flexible elongate atmospheric plasma generator 4, there are transverse cross-sections through at least 4, optionally from 4 to 16, of the electrically conductive elements 16 which are spaced from each other around an external circumference of the body 8 of dielectric material. In the embodiment of FIGS. 1 to 4, the second electrode 12 comprises an electrically conductive knitted wire mesh 20 wrapped around the elongate external surface 14 of the body 8 of dielectric material.

The mesh 20 is configured so that when the plasma generator 4 is electrically powered a surface dielectric barrier discharge (DBD) is achieved in the holes 21 between the first electrode 10 and the electrically conductive elements 16 of the second electrode 12, thereby generating a transverse plasma in atmospheric air.

In one preferred embodiment of the present invention, the first electrode 10 has a diameter of 0.6 mm, the body 8 of dielectric material has an external diameter of 2 mm, there are sixteen elements 16 in a transverse cross-section of the plasma generator 4 and the elements have a width, tangential to the circumferential direction the plasma generator 4, of 0.2 mm.

Figure 3:
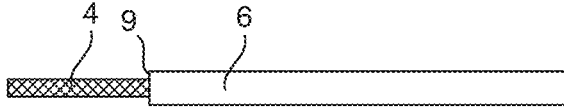
FIG. 3 is a perspective view of the flexible elongate atmospheric plasma generator illustrated in FIG. 1 after insertion into an elongate endoscope tube for sterilising the interior surface of the endoscope tube in accordance with an embodiment of the method of the present invention.
Figure 4:
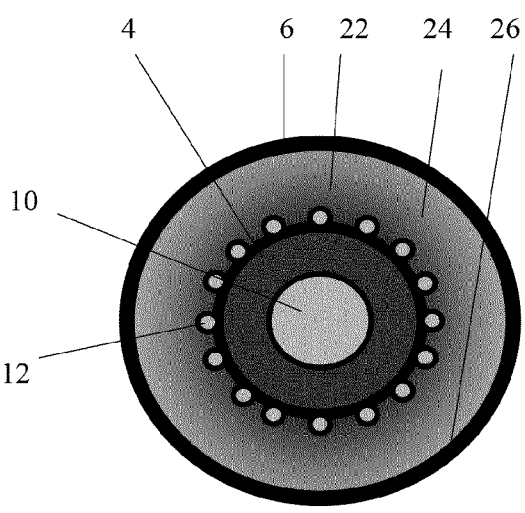
FIG. 4 is a transverse cross-section through the flexible elongate atmospheric plasma generator after insertion into an elongate endoscope tube as illustrated in FIG. 3.

As shown in FIGS. 3 and 4, in use the plasma generator 4 is inserted into an elongate endoscope tube 6. The flexible elongate atmospheric plasma generator 4 is configured for insertion into an open end 9 of, and along a length of, an internal channel 24 of the elongate endoscope tube 6. The plasma generator 4 is provided with width and length dimensions which match the internal diameter and length of the endoscope tube 6 to be sterilise with the proviso that as shown in FIG. 4 the width of the plasma generator 4 is less than the width of the endoscope tube 6 to enable the plasma generator 4 to be surrounded by an annulus 22 of atmospheric air within the internal channel 24 of the endoscope tube 6 which is defined by the interior cylindrical surface 26 of the endoscope tube 6. The plasma generator 4 is configured such that application of a potential difference across the first and second electrodes 10, 12 can generate a transverse atmospheric plasma within atmospheric air surrounding the plasma generator 4.

As described hereinbelow, in use the plasma generator 4 is electrically powered to form an atmospheric plasma within the annulus 22 of atmospheric air within the internal channel 24 of the endoscope tube 6, thereby sterilising the cylindrical surface 26 of the endoscope tube 6.

Typically, a range of plasma generators 4 having different widths may be provided for use in sterilising a corresponding range of endoscope tubes 6 of different widths.

Figure 5:
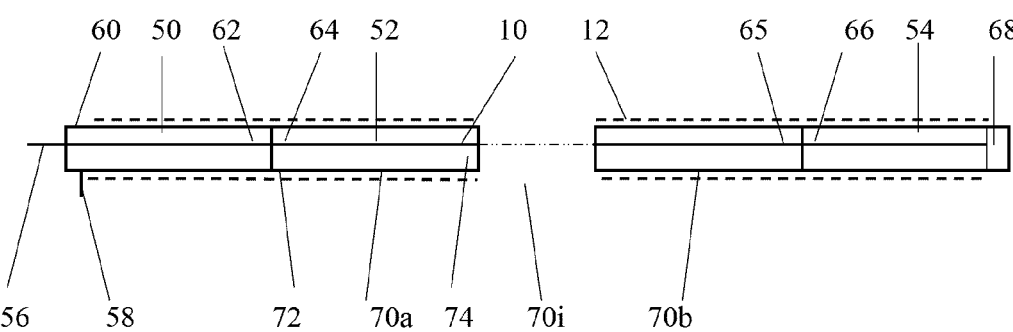
FIG. 5 is a schematic longitudinal cross-section through the flexible elongate atmospheric plasma generator illustrating a modular system comprising a series of modules of the flexible elongate atmospheric plasma generator.
Figure 6:
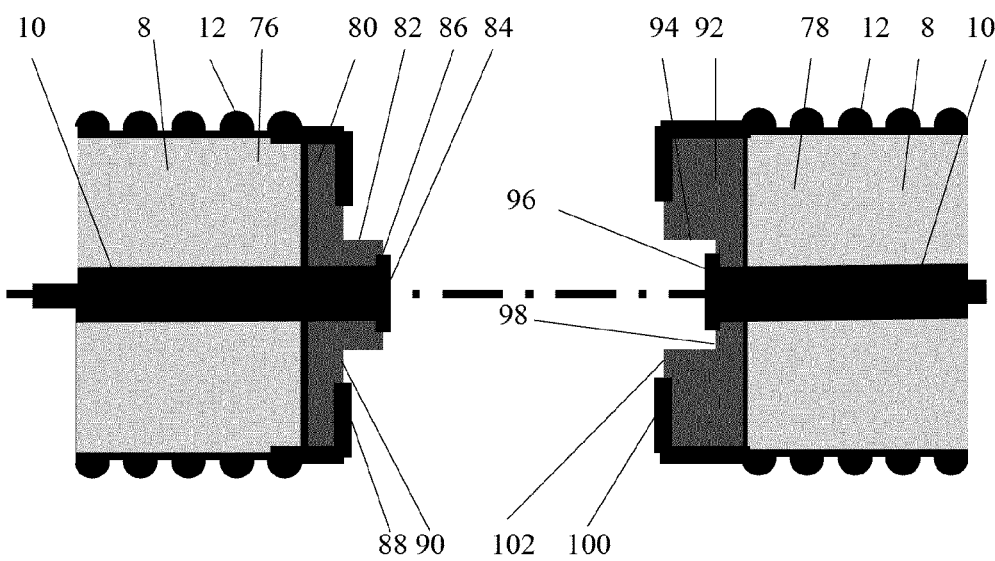
FIG. 6 is a schematic longitudinal cross-section through a part of the flexible elongate atmospheric plasma generator illustrated in FIG. 5, FIG. 6 illustrating an interlocking electrical connection between two adjacent modules of the flexible elongate atmospheric plasma generator.

Referring to FIGS. 5 and 6, there is illustrated an interlocking electrical connection between two adjacent modules of the flexible elongate atmospheric plasma generator 4, which modular system enables the length of the plasma generator 4 to be adjusted to correspond to the length of any give elongate endoscope tube 6 to be sterilised by the plasma generator 4.

As shown in FIGS. 5 and 6, the atmospheric plasma generator 4 comprises a plurality of elongate modules 50, 52, 54 which are connectable along a length direction to form the elongate atmospheric plasma generator 4.

The elongate modules 50, 52, 54 comprise a first end module 50 comprising a pair of first and second electrical connectors 56, 58 each connected to a respective one of the first and second electrodes 10, 12. The pair of first and second electrical connectors 56, 58 are located at a first end 60 of the first end module 50. The first end module 50 has a second end opposite 62 to the first end 60.

A central module 52 has a first end 64 for interlocking electrical connection to the second end 62 of the first end module 50 and an opposite second end 65.

A second end module 54 comprises a first end 66 for interlocking electrical connection to the second end 65 of the central module 52 and an opposite second end 68 which is electrically insulated, and typically formed from the body 8 of dielectric material.

The central module 52 preferably comprises a plurality of sub-modules 70 which are connectable along the length direction to form the central module 52. FIG. 5 shows two sub-modules 70a and 70b, and optionally one or more additional sub-modules 70i may be disposed therebetween. However, only one sub-module 70 may be provided, in which case the central module 52 consists of a single sub-module 70.

Each sub-module 70 has a first end 72 and a second end 74. The first end 72 is for interlocking electrical connection to the second end 62 of the first end module 52 or to a second end 74 of another sub-module 70. The second end 74 is for interlocking electrical connection to the first end 66 of the second end module 54 or to a first end 72 of another sub-module 70.

As shown in detail in FIG. 6, each interlocking electrical connection is between a pair of male and female ends 76, 78 of the respective elongate modules 50, 52, 54, or submodules 70.

The male end 76 comprises a first transverse layer 80 of electrically insulating material comprising a central projection 82 surrounding the first electrode 10 of the respective module 50, 52, 54, or submodule 70. A transverse first central contact plate 84 is electrically connected to the first electrode 10 and disposed on an end surface 86 of the central projection 82. A transverse first peripheral contact plate 88 is electrically connected to the second electrode 12 of the respective module 50, 52, 54, or submodule 70. The first peripheral contact plate 88 is disposed on an end surface 90 of the first transverse layer 80 and is located radially outwardly from the first central contact plate 84.

The female end 78 comprises a second transverse layer 92 of electrically insulating material comprising a central recess 94 surrounding the first electrode 10 of the respective module 50, 52, 54, or submodule 70. A transverse second central contact plate 96 is electrically connected to the first electrode 10 and disposed on an inner end surface 98 of the central recess 94. A transverse second peripheral contact plate 100 is electrically connected to the second electrode 12 of the respective module 50, 52, 54, or submodule 70, The second peripheral contact plate 100 is disposed on an end surface 102 of the second transverse layer 92 and is located radially outwardly from the second central contact plate 96.

The first and second central contact plates 84, 96 have the same shape and dimensions and are preferably circular. The first and second peripheral contact plates 88, 100 have the same shape and dimensions and are preferably annular.

When the pair of male and female ends 76, 78 form an interlocking electrical connection, the first and second central contact plates 84, 96 are urged into electrical contact, and the first and second peripheral contact plates 88, 100 are urged into electrical contact. The pair of male and female ends 76, 78 may be held together by a press-fitting or a compression fitting, or by any other interlocking mechanism, for example a magnetic coupling, a push-pull coupling, a screw-threaded coupling, or any other suitable coupling mechanism (not shown) is.

It may be seen that using this modular system, the flexible elongate atmospheric plasma generator 4 may be assembled from a plurality of modules to have a desired length in order to fit the length of the flexible elongate atmospheric plasma generator 4 to a given endoscope tube 6 to be sterilised. The flexible elongate atmospheric plasma generator 4 comprises a first end module 50 for connection to the source of electrical power, a second end module 54 having a free second end 68 which is electrically insulated, and a central module 52 comprising either a single central module 52 or one or more sub-modules 70. The electrical connections between the modules 50, 52, 54, and sub-modules 70 when present, ensure that electrical power is uniformly provided along the extended length of the first and second electrodes 10, 12 and that an atmospheric plasma is uniformly and homogeneously generated along the length of the flexible elongate atmospheric plasma generator 4 so that the entire length of a given endoscope tube 6 can be uniformly, consistently and reliably sterilised.

Figure 7:
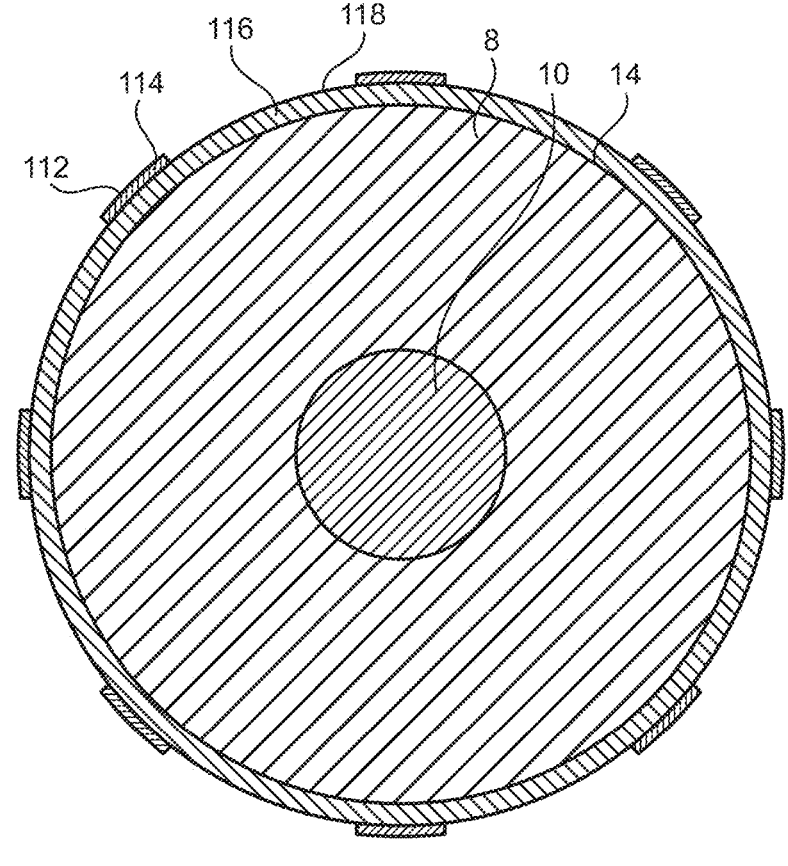
FIG. 7 is a transverse cross-section through a flexible elongate atmospheric plasma generator in accordance with a second embodiment of the apparatus of the present invention.
Figures 8A, 8B:
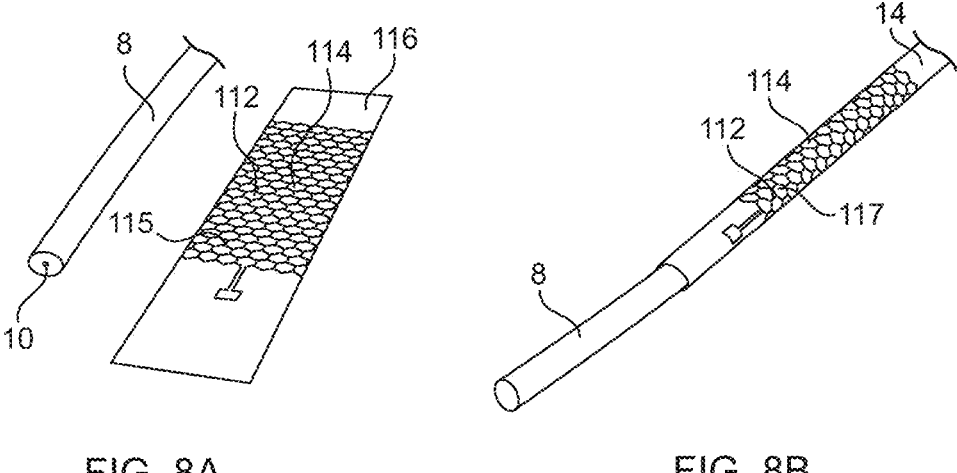
FIGS. 8a and 8b are perspective views of the flexible elongate atmospheric plasma generator illustrated in FIG. 7 respectively prior to, and subsequent to, assembly of the flexible elongate atmospheric plasma generator.

Referring to FIGS. 7, 8a and 8b, there is illustrated an apparatus for sterilising an interior surface of an elongate endoscope tube by an atmospheric plasma in accordance with a second embodiment of the present invention.

In the second embodiment of the present invention, the second electrode has a different construction as compared to the first embodiment. Also, the width dimensions of the plasma generator of the second embodiment may be smaller as compared to the first embodiment. However, other features may be commonly present in both of the first and second embodiments.

As shown in FIGS. 7, 8a and 8b, the second electrode 112 comprises an electrically conductive mesh 114 printed on an electrically insulating substrate 116, which is preferably flexible. The mesh 114 comprises a plurality of electrically conductive elements 115 defining holes 117 in the second electrode 112. The mesh 114 is in the form of a regular hexagonal array, although other regular arrays may be employed. At least some of the elements 115 are oriented in a helical direction around the elongate external surface 14 of the body 8 of dielectric material. The mesh 114 is configured so that when the plasma generator is electrically powered a surface dielectric barrier discharge (DBD) is achieved in the holes 117 between the first electrode 10 and the electrically conductive elements 115 of the second electrode 112, thereby generating a transverse plasma in atmospheric air.

As shown in FIG. 8a, initially the electrically insulating substrate 116 may be planar to facilitate printing of the electrically conductive mesh 114 onto an outer surface 118 of the electrically insulating substrate 116. Then, as shown in FIG. 8b, the flexible substrate 116 is wrapped around the elongate external surface 14 of the body 8 of dielectric material. Such wrapping provides the second electrode 112 over the outer surface 118 of the electrically insulating substrate 116.

Typically, the electrically insulating substrate 116 comprises a polyimide film. In preferred embodiments, the printed electrically conductive mesh 114 has a thickness of from 0.01 to 0.1 mm and/or the electrically insulating substrate has a thickness of from 0.025 to 0.1 mm. In one preferred embodiment, the printed electrically conductive mesh 114 has a thickness of 0.01 mm and the electrically insulating substrate has a thickness of 0.025 mm. In one preferred embodiment, these dimension ranges and the preferred dimensions may be used in combination with a first electrode 10 having a width of 0.6 mm and a body 8 of dielectric material having a width of 2 mm.

The flexible elongate atmospheric plasma generator of the first embodiment comprises a knitted meshed grounded electrode as the second electrode, which provides a longer lifetime of the plasma generator, and a higher manufacturing cost, as compared to the use of a printed grounded electrode as used in the second embodiment. This plasma generator of the first embodiment is suitable for endoscopes which have relatively larger lumens and channel diameter, and typically also are frequently used, thereby requiring many repeated sterilisation processes. The flexible elongate atmospheric plasma generator of the second embodiment uses a printed grounded electrode which is much thinner and lighter than the knitted meshed grounded electrode of the first embodiment. The use of a conventional printing technique as used in electronics manufacturing to produce the printed grounded electrode, the plasma generator is less expensive to manufacture. However, the lifetime of the plasma generator is shorter than for the first embodiment. The use of a printed grounded electrode provides the technical advantage that a highly controllable and uniform plasma is generated due to the manufacturing precision of the printing process. Thus, the structure of the second embodiment is more suitable for a high-end expensive endoscope which uses sensitive materials, and also an endoscope having very small lumens and channels, for example below 2 mm in internal diameter.

Figure 11:
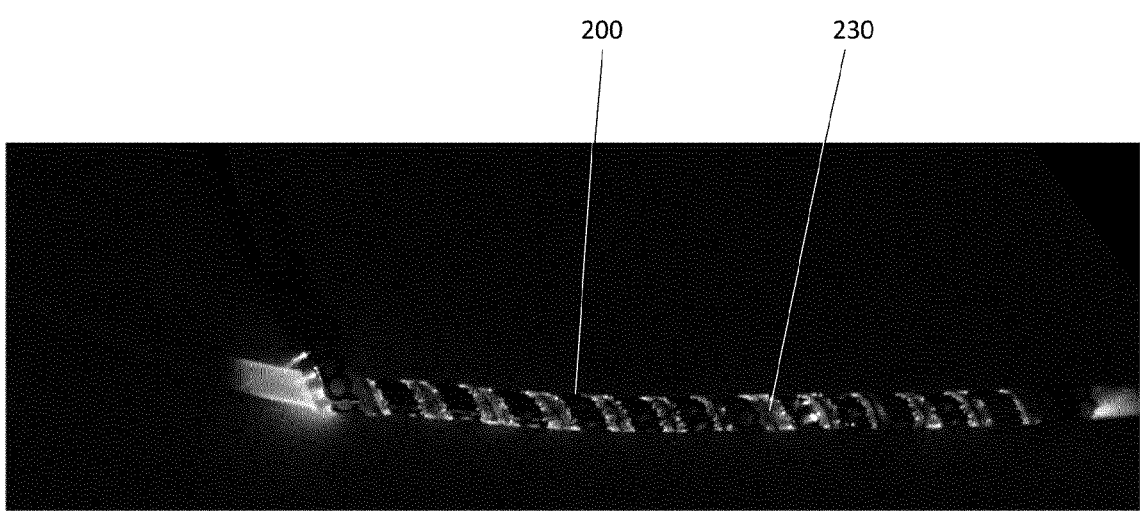
FIG. 11 is a perspective view of the flexible elongate atmospheric plasma generator illustrated in FIG. 9 after ignition to generate a plasma.

FIGS. 9 to 11 illustrate a flexible elongate atmospheric plasma generator 200 in accordance with a third embodiment of the present invention. This embodiment has a "hybrid" electrode system which can provide an improvement over the knitted electrode of the first embodiment and the printed electrode of the second embodiment. In this embodiment, the "hybrid" electrode system is a coaxial electrode system consisting of a fully insulated power electrode 202, at the axial centre of the flexible elongate atmospheric plasma generator 200, and a printed ground electrode 204 coaxially disposed around the fully insulated power electrode 202.

The elongate power electrode 202 is centrally located within a body 206 of dielectric material. The power electrode 202 and the body 206 of dielectric material are coaxial. As for the first embodiment, the power electrode 202 is typically composed of a flexible metal wire, typically comprising a plurality of wire filaments, and the power electrode may have the same shape and dimensions as the first electrode of the first embodiment. As illustrated, the power electrode 202 is preferably circular in transverse cross section.

The ground electrode 204 comprises an electrically conductive mesh 208 printed on an electrically insulating substrate 210, which is flexible. The mesh 208 comprises a plurality of electrically conductive elements 220 defining holes 222 in the ground electrode 204. The mesh 208 is typically covered by a layer of protective coating 212, for example composed of a polymer or a varnish, so that the electrically conductive elements 220 are sandwiched between the electrically insulating substrate 210 and the protective coating 212. The ground electrode 204 is formed as an elongate strip 216 which is helically wrapped around the body 206 of dielectric material. Preferably, the ground electrode 204 is bonded to the body 206 of dielectric material. The mesh 208 is in the form of a regular hexagonal array, although other regular arrays may be employed. Accordingly, the electrically conductive elements 220 are oriented in a helical direction around the elongate external surface 224 of the body 8 of dielectric material.

In the illustrated embodiment, the electrically insulating substrate 210 is wrapped against the body 8 of dielectric material and the layer of protective coating 212 defines the outer circumferential surface of the flexible elongate atmospheric plasma generator 200. The protective coating can improve the efficiency and reliability of the plasma source during long-term application. In an alternative embodiment, the layer of protective coating 212 is omitted, the electrically conductive elements 220 are wrapped against the body 8 of dielectric material, and the electrically insulating substrate 210 defines the outer circumferential surface of the flexible elongate atmospheric plasma generator 200.

The mesh 208 is configured so that when the plasma generator is electrically powered a surface dielectric barrier discharge (DBD) is achieved in the holes 222 between the power electrode 202 and the electrically conductive elements 220 of the ground electrode 204, thereby generating a transverse plasma in atmospheric air.

Typically, the electrically insulating substrate 210 comprises a polyimide film, for example composed of a polyimide film sold under the trade mark Kapton®. In preferred embodiments, the printed electrically conductive mesh 208 has a thickness of from 0.01 to 0.1 mm and/or the electrically insulating substrate 210 has a thickness of from 0.025 to 0.1 mm. In one preferred embodiment, the printed electrically conductive mesh 208 has a thickness of 0.01 mm and the electrically insulating substrate 2010 has a thickness of 0.025 mm. In one preferred embodiment, these dimension ranges and the preferred dimensions may be used in combination with a power electrode 202 having a width of 0.6 mm and a body 8 of dielectric material having a width of 2 mm.

As for the second embodiment, the use in the third embodiment of a printed ground electrode comprising very thin layer minimizes the weight of the hybrid electrode system in comparison to the use of a knitted electrode. The printed ground electrode of the hybrid electrode system can improve the uniform plasma generation by reducing the deformation of ground electrode and improve the omnidirectional flexibility of a plasma system by employing a coaxial configuration. FIG. 11 shows the flexible elongate atmospheric plasma generator after ignition to generate a plasma, and it can be seen that the plasma 230 is uniform at the location of the mesh 208.

The elongate atmospheric plasma generator of the illustrated embodiments of the present invention is flexible. The flexibility of the system plasma generator is an essential feature to treat a flexible endoscope. As all endoscope lumen and channels are flexible, in contrast a rigid plasma generator would need to deform an endoscope to urge it into a straight line configuration, which would require unnecessary excess preparation time for reprocessing the endoscope, i.e. sterilising the endoscope after use on a patient to make the endoscope sterile for a subsequent healthcare application. A flexible elongate atmospheric plasma generator allows the operator to directly insert the plasma generator into an endoscope without maintaining the shape of an endoscope. Thus, the flexible elongate atmospheric plasma generator of the illustrated embodiments of the present invention can reduce the reprocessing time by minimising preparation time.

Figure 12:
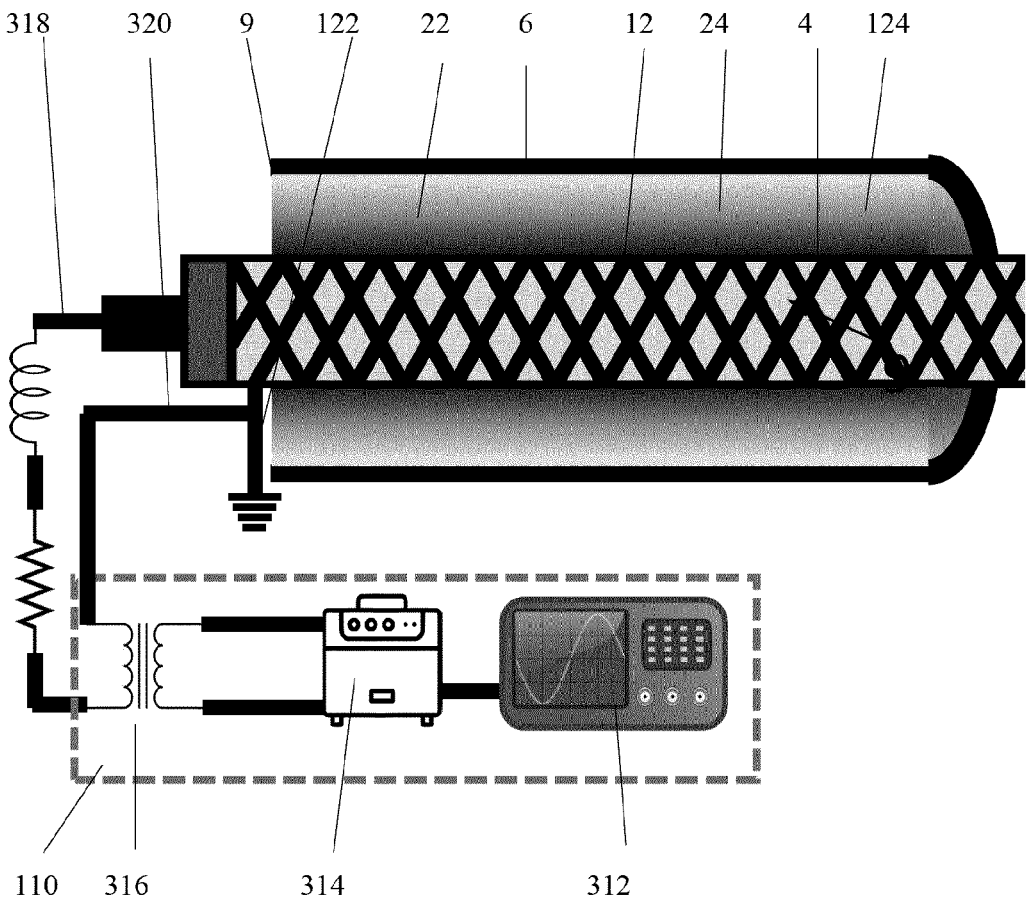
FIG. 12 schematically illustrates the apparatus of the present invention comprising the flexible elongate atmospheric plasma generator illustrated in FIG. 1 when used to sterilise the interior surface of an elongate endoscope tube by an atmospheric plasma in accordance with an embodiment of the method of the present invention.

Referring to FIG. 12, there is illustrated an apparatus for sterilising an interior surface of an elongate endoscope tube by an atmospheric plasma which comprises the flexible elongate atmospheric plasma generator of any of the first, second and third embodiments of the present invention illustrated in FIGS. 1 to 11.

As shown in FIG. 12, the apparatus further comprises an electrical power supply 110 for supplying electrical power to the flexible elongate atmospheric plasma generator 4 to cause the plasma generator 4 to generate a transverse atmospheric plasma 124 in the endoscope tube 6 homogeneously throughout the annulus 22 of atmospheric air within the internal channel 24 of the endoscope tube 6.

The electrical power supply 110 comprises a control system 312 for controlling the voltage, current and frequency of an alternating current electrical power output, a power amplifier 314 for amplifying the output of the control system 312 and transformer 316 for converting the input voltage and current to a desired high voltage and low current power output. First and second power terminals 318, 320 are respectively connected to the first and second electrodes 10, 12. Typically, the second electrode 12 is connected to a ground terminal 122. One or more resistors/inductors may be located in the circuit between the transformer 316 and the first electrode 10 to control the power output fed to the first electrode 10.

The control system 312 is adapted to supply electrical power preferably having a frequency of from 1 to 10 kHz, optionally 2+/–0.5 kHz. The peak-to-peak (pp) voltage is preferably from 5 to 15 kVpp, optionally 9+/–2 kVpp. The control system 312 is preferably configured to supply a low current to the flexible elongate atmospheric plasma generator 4 in order to enhance the safety of the apparatus when used to sterilise endoscope tubes 6. Preferably, the control system 312 is adapted to provide electrical power having a current of from 0.5 to 4 mA, optionally 1.5+/–0.5 mA. In one example, the flexible elongate atmospheric plasma generator 4 is powered by a voltage of 2 kHz at a current of from 1-2 mA, and a voltage of 10 kHz for the embodiment of FIGS. 1 to 4 having a knitted second grounded electrode and a voltage of 8 kHz for the embodiment of FIGS. 7 to 8b having a printed second grounded electrode.

However, health care workers can adjust the operating parameters, such as the electrical input, output voltage and output current and output frequency to meet their specific health care needs, and so the plasma generator of the preferred embodiments is readily adjustable and therefore very flexible to be used to sterilise different endoscopes, having different dimensions, materials and contaminants. In contrast, current chemical-based decontamination methods are inflexible and it is difficult accurately to modify the chemical decontamination process for reliable sterilisation of different endoscopes, having different dimensions, materials and contaminants. This is one of key technical advantages of the plasma generator of the preferred embodiments.

Based on the type of contaminants, the level of contamination and the material of an endoscope channel, the operator can control the strength of decontamination by simply adjusting the voltage and the frequency to meet their specific needs, based upon prior results.

Preferably, the current is limited to be below about 1~2 mA for safety. The power consumption is typically about 8 W for a plasma generator having an operating length of about 1 metre, for sterilising an endoscope having a length of about 1 metre. The power output can be varied by changing the output (voltage and frequency using the control system.

The apparatus of the first and second embodiments is used in a method of sterilising an interior surface of an elongate endoscope tube by an atmospheric plasma.

In the method, an apparatus of the first and second embodiments is provided. The flexible elongate atmospheric plasma generator 4 is inserted into an elongate endoscope tube 6 so that the elongate second electrode 12 is in contact with atmospheric air within the elongate endoscope tube 6. Then electrical power is supplied to the flexible elongate atmospheric plasma generator 4 by the control system 312 to cause the plasma generator 4 to generate a transverse atmospheric plasma within the elongate endoscope tube 6.

The elongate endoscope tube 6 may be any known endoscope tube 6 used in healthcare. For example, the elongate endoscope tube 6 is composed of a flexible polymer, for example polypropylene. Typically, the elongate endoscope tube 6 has a length of at least 50 cm, optionally from 1 to 3 metres, further optionally from 1 to 2 metres. The elongate endoscope tube 6 may have any internal diameter which is suitable for any known endoscope tube 6 used in healthcare. For example, the elongate endoscope tube 6 may have an internal diameter of from 1.5 to 10 mm, optionally from 2 to 5 mm, further optionally from 2 to 3 mm.

Typically, the flexible elongate atmospheric plasma generator 4 extends along at least 100%, preferably at least 105%, more preferably at least 110%, of the length of the elongate endoscope tube 6.

Typically, the transverse atmospheric plasma is generated within the elongate endoscope tube 6 for a sterilisation treatment period of from 1 to 10 minutes, optionally from 1 to 5 minutes.

After use, the flexible elongate atmospheric plasma generator can readily be cleaned and decontaminated. The flexible elongate atmospheric plasma generator itself has a self-decontamination capability because it generates a plasma over the entire surface of the plasma generator. After using the plasma generator for decontaminating an endoscope, the operator can simply wash the exterior surface of the plasma generator system using a suitable cleaning tool or ultrasonic bubbles to remove any large debris, for example biological tissues or proteins, from the surface. Then, the plasma generator can self-sterilise by operating the plasma generator in ambient air for a decontamination treatment period of from 2 to 5 minutes. This decontamination procedure ensures the plasma generator is safe to use for subsequently sterilising another endoscope.

Since the plasma generator does not use any chemical disinfectants, the plasma generator does not produce any chemical residues and waste which, in contrast in known sterilisation procedures, often cause environmental issues within hospitals, such as increasing the antimicrobial resistance (AMR) of bacteria.

EXAMPLES

The apparatus and method of the present invention are further described with reference to the following non-limiting examples.

Example 1

An endoscope tube contaminated with *Pseudomonas* bacteria was sterilised using a plasma generator in accordance with the present invention.

The plasma generator had the structure of the first embodiment, with an external diameter of about 2 mm inserted into an endoscope tube of 2.5 mm internal diameter, and using a voltage of 10 kVpp, a current of 1-2 mA and a frequency 2 kHz to generate a transverse atmospheric plasma within the endoscope tube.

*Pseudomonas* is a bacteria having antibiotic resistance, and is quite difficult to inactivate using bactericide, and moreover the use of a chemical-based bactericide can increase its antibiotic resistance.

The test result showed that the plasma generator in accordance with the present invention can inactivate *Pseudomonas* bacteria using a sterilisation treatment period of 5 minutes.

When a sterilisation treatment period of 10 minutes was employed, after a further period of 72 hours the growth of *Pseudomonas* bacteria was very low. This test result confirms that the plasma generator in accordance with the present invention can inactivate viable but nonculturable (VBNC) bacteria. VNBC bacteria are in a state of very low metabolic activity and do not divide, but are alive and have the ability to become culturable once resuscitated.

Example 2

An endoscope tube contaminated with *Enterococcus* bacteria was sterilised using a plasma generator in accordance with the present invention. The test result showed that the plasma generator in accordance with the present invention can inactivate *Enterococcus* bacteria using a sterilisation treatment period of 2 minutes.

Thus, the results of Examples 1 and 2, on *pseudomonas* and *enterococcus* respectively, exhibit the decontamination capability of the plasma generator in accordance with the present invention against various type of bacteria.

Example 3

A plasma generator in accordance with the present invention, having the structure of the embodiment of FIG. 1, was tested to determine the uniformity of plasma generation along the length of the plasma generator.

The strength of plasma is proportional to the luminous intensity of plasma discharge. Consequently, the uniformity of generated plasma was assessed using image processing.

The elongate plasma generator was divided into a series of evaluation sections along the length of the plasma generator. For each evaluation section, an image intensity value, $I_{img}$, was obtained as:

$$I_{img} = \sum_{i=1}^{n}\sum_{j=1}^{m} R_{ij} + \sum_{i=1}^{n}\sum_{j=1}^{m} G_{ij} + \sum_{i=1}^{n}\sum_{j=1}^{m} B_{ij}$$

where $R_{ij}$, $G_{ij}$, $B_{ij}$ are the measured pixel intensities of the respective red (R), green (G) and blue (B) parts of the image of the evaluation section, and n and m are the width and height of the imaged evaluation section, respectively.

Figure 13:
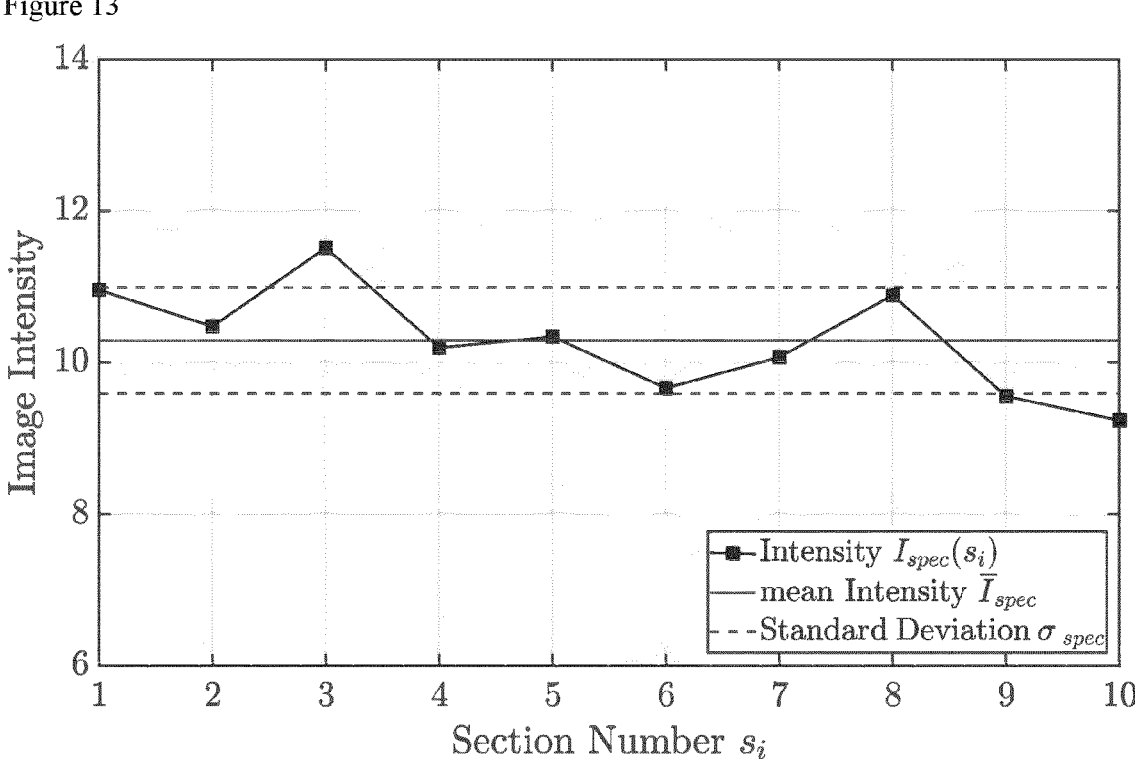
FIG. 13 is a graph illustrating the relationship between the intensity of an image of the plasma and length along the flexible elongate atmospheric plasma generator illustrated in FIG. 1.

The mean image intensity, $\bar{I}_{img}$ was defined as the average intensity along all evaluation sections of the plasma generator. The mean image intensity was used to quantify the overall intensity of the generated plasma. The standard deviation, $\sigma_{img}$, along all evaluation sections indicated the uniformity of the generated plasma along the plasma generator The result is shown in FIG. 13 which shows the quantified plasma intensity using the image processing approach. As can be seen, the plasma generated by the elongate plasma generator according to the present invention has small variations in the mean intensity.

Example 4

The composition, and chemical properties, of the generated plasma from the elongate plasma generator according to the present invention were analysed using optical emission spectroscopy (OES). The intensity of the emitted light from the generated plasma was measured within the wavelength range of from the 200 nm to 1100 nm using an Ocean Optics® HR-4000 spectrometer coupled with a 100 µm optical fibre. Emission spectra were recorded in a physical area of approx. 4.5 mm² over an integrated time period of 30 seconds.

Figure 14:
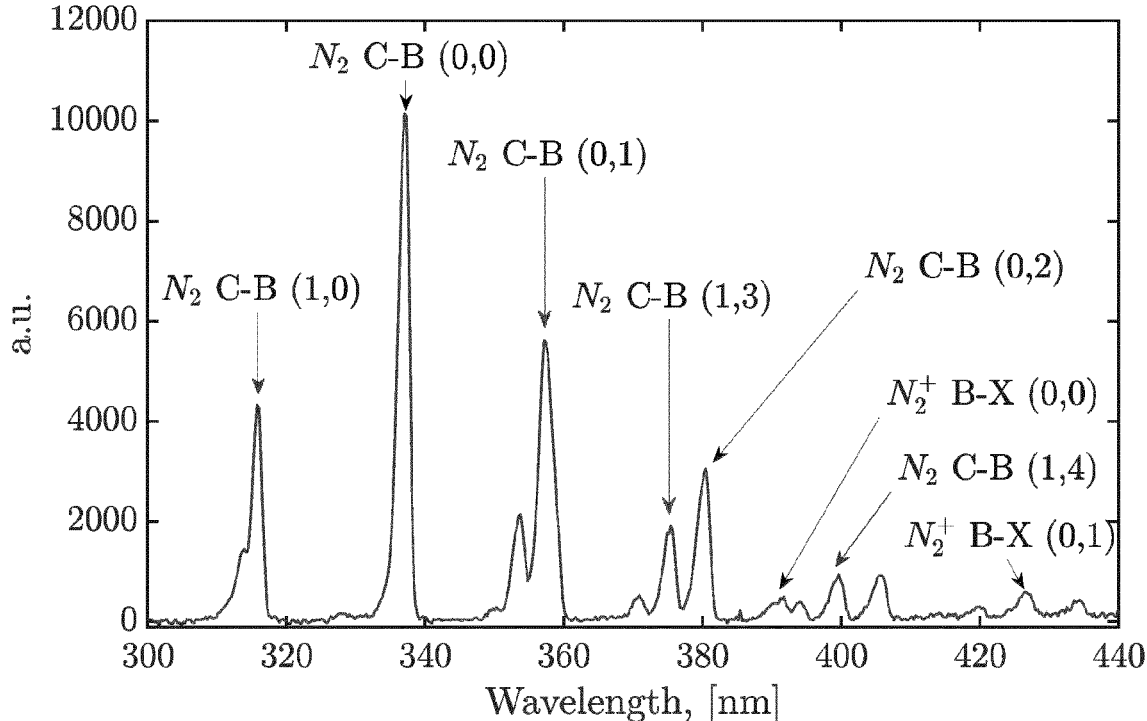
FIG. 14 is a graph illustrating the emission spectrum of the atmospheric plasma generated by the flexible elongate atmospheric plasma generator illustrated in FIG. 1.

The result is shown in FIG. 14 which shows the recorded spectra from the plasma emission. The major emission peaks of the second positive system of $N_2$ (C-B) and the first negative system of $N_2^+$(B-X) can be seen in the wavelength range from 300 to 440 nm. As the generated plasmas have mean electron energies in the range of few eV, only a small fraction of electrons possessed energies that exceed these elementary processes. Therefore, the relative low intensity of $N_2^+$(B-X) at 391 nm is indicative of this small number of highly energetic electrons. The emission of atomic oxygen at 777 nm and 845 nm can currently not been detected, even though the required energy for these transitions is well below the threshold for emission at 391 nm. This is mainly due to high quenching rates from collisions with N2 and O2 molecules. The spectra of generated plasma at various locations using the elongate plasma generator according to the present invention show similar patterns of emission peaks, which confirms that the elongate plasma generator according to the present invention can provide the similar chemical composition of the plasma along the entire system.

Example 5

In this Example, the scalability of the modular elongate plasma generator according to the present invention, for example as described above with reference to FIGS. 5 and 6, was tested.

A test configuration was used for testing the modular elongate plasma generator, which consisted of various electrical and optical diagnostic tools, such as voltage and current sensor, a CMOS sensor and optical emission spectroscopy (OES). The electrical characteristics of the modular elongate plasma generator were quantified to determine the power intensity of the generated plasma using electrical diagnostics. The average power consumption, Pave, of the modular elongate plasma generator was obtained by evaluating the area inside a Lissajous curve as:

$$P_{ave} = \frac{1}{T}\oint_T V(t)dQ$$

The power intensity was used as a basic parameter to characterize the electrical properties of the generated plasma because a varying power intensity measurement can indicate varying plasma properties. The spectral intensity was measured using optical emission spectroscopy.

Figure 15:
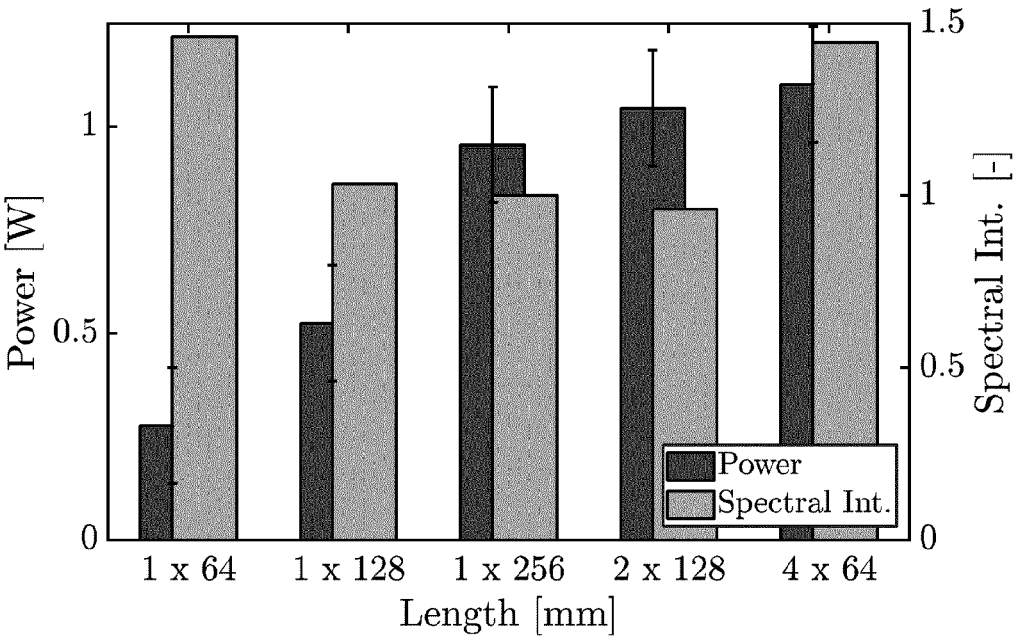
FIG. 15 is a graph illustrating the relationship between both power and spectral intensity with respect to length of a modular flexible elongate atmospheric plasma generator, when arranged in series or in parallel, as illustrated in FIGS. 5 and 6.

The results are shown in FIG. 15 which shows the measured power consumption and spectral intensity when modules of the elongate plasma generator were combined in series or in parallel, to provide various lengths of the resultant modular elongate plasma generator. As can be seen, the power intensities per unit length for varying lengths of the modular elongate plasma generator remain mostly constant, within the range of from about 3.75 to about 4.22 W/m, there being some fluctuations due to measurement uncertainty.

Example 6

The biological decontamination capability of the elongate plasma generator according to the present invention was evaluated by looking at the profiles of bacterial growth after an operation to generate a plasma within an endoscope channel. An endoscope channel was modelled using a PTFE (Polytetrafluoroethylene) tube having 2.5 mm internal radius. The test endoscope channels were sterilised before controlled contamination. The test endoscope channels were then contaminated under otherwise sterile conditions with suspension cultures of *Enterococcus* (VRE strain) and *Pseudomonas* (P001 strain) using a sterile syringe sealed to one end of the channel. After a contact time of one-hour, non-adhesive bacteria were flushed out by pumping sterile water through the contaminated channel. The contaminated channels were incubated at 37° C. for up to 72 hours to allow biofilm growth before treatment and/or examination.

Both control and plasma-treated samples were examined for the presence of any residues using highly sensitive episcopic fluorescence microscopy (EDIC/EF). Control and plasma-treated test samples were rinsed with sterile water using a sealed syringe to remove any unattached bacteria, then cut open longitudinally for direct observation of the luminal surface under EDIC/EF microscopy which can detect single bacterial cells if present. Biofilms were labelled using fluorescent stains to assess total biomass (using the dye SYPRO Ruby) and viability (Live/dead staining using SYTO9/Propidium iodide or measure of dehydrogenase activity using TTC). The fluorescent signal captured with a digital camera was quantified by an image analysis software.

Figure 16:
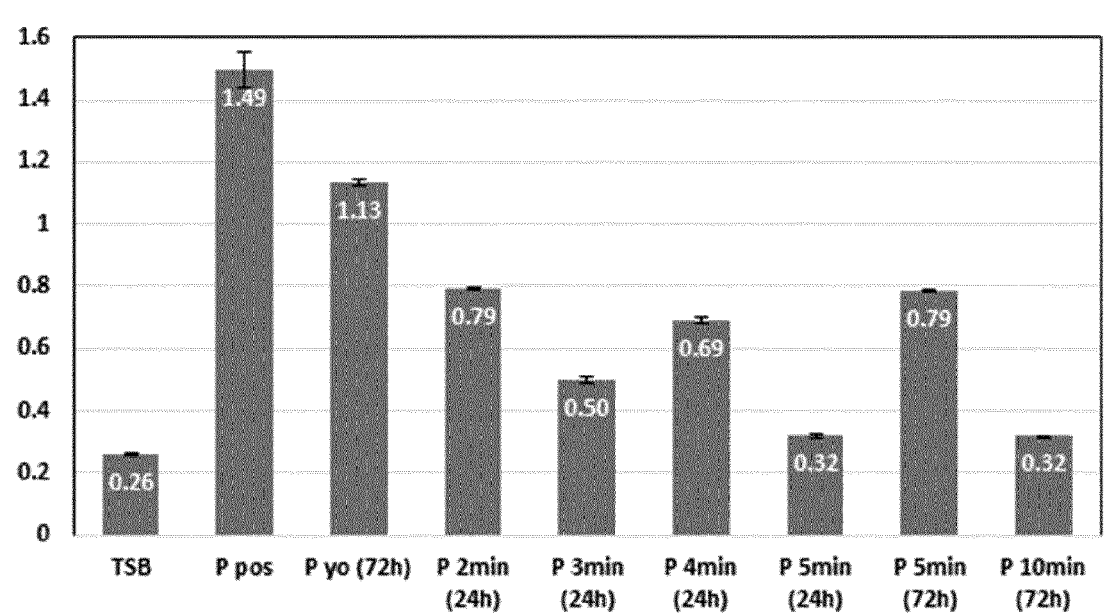
FIGS. 16 and 17 are graphs showing the treatment of bacteria, respectively the *Pseudomonas* (P001 strain) and the *Enterococcus* (VRE strain), using the elongate atmospheric plasma generator according to the present invention.
Figure 17:
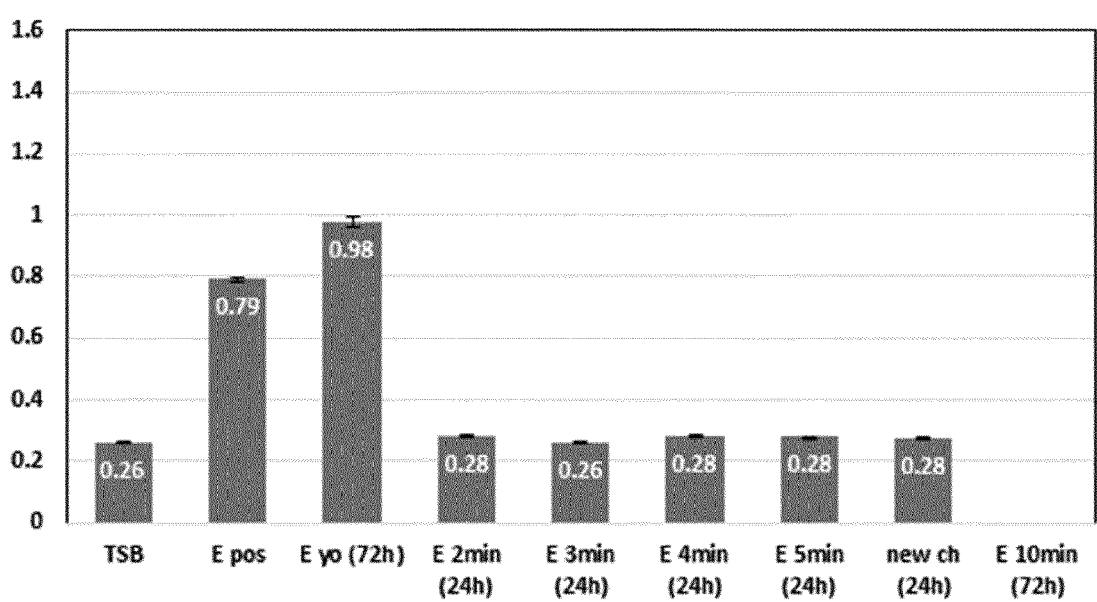

The results are shown in FIG. 16 for the *Pseudomonas* (P001 strain) and FIG. 17 for the *Enterococcus* (VRE strain).

Some of the treated samples were left growing for 72 hours and P001 appeared to recover. After plasma treatment for a period of 10 minutes using the elongate plasma generator according to the present invention, there was limited regrowth even after 72 hours incubation in TSB. For *enterococcus*, the results show apparent "kill" straight from 2 minutes of the plasma treatment.

The invention claimed is:

1. An apparatus for sterilising an interior surface of an elongate endoscope tube by an atmospheric plasma, the apparatus comprising a flexible elongate atmospheric plasma generator for generating a transverse atmospheric plasma within, and along a length of, an elongate endoscope tube into which the atmospheric plasma generator has, in use, been inserted, the flexible elongate atmospheric plasma generator being configured for insertion into an end of, and along a length of, an internal channel of an elongate endoscope tube, the flexible elongate atmospheric plasma generator comprising an elongate body of dielectric material, an elongate first electrode centrally located within the body of dielectric material and an elongate second electrode around an elongate external surface of the body of dielectric material, wherein the second electrode comprises a plurality of electrically conductive elements forming a mesh defining holes in the second electrode, wherein the second electrode comprises an electrically conductive mesh printed on an electrically insulating substrate, and the substrate is wrapped around the elongate external surface of the body of dielectric material, and wherein the atmospheric plasma generator is configured such that application of a potential difference across the first and second electrodes can generate a plasma within atmospheric air surrounding the atmospheric plasma generator.

2. The apparatus according to claim 1 wherein the plurality of electrically conductive elements form a regular array surrounding the elongate external surface of the body of dielectric material.

3. The apparatus according to claim 2 wherein at least some of the elements are oriented in a helical direction around the elongate external surface of the body of dielectric material.

4. The apparatus according to claim 2 wherein each element has a width, measured in a circumferential direction around the plasma generator, or tangential to the circumferential direction, of from 0.1 to 0.5 mm.

5. The apparatus according to claim 4 wherein the width is from 0.1 to 0.3 mm.

6. The apparatus according to claim 2 wherein in a transverse cross-section through the plasma generator, there are transverse cross-sections through at least 4 of the electrically conductive elements which are spaced from each other around an external circumference of the body of dielectric material.

7. The apparatus according to claim 6 wherein in a transverse cross-section through the plasma generator, there are transverse cross-sections through from 4 to 16, of the electrically conductive elements which are spaced from each other around an external circumference of the body of dielectric material.

8. The apparatus according to claim 1 wherein the electrically insulating substrate comprises an elongate strip which is helically wrapped around the elongate external surface of the body of dielectric material.

9. The apparatus according to claim 1 wherein the electrically conductive mesh is in the form of a regular hexagonal array.

10. The apparatus according to claim 1 wherein the second electrode further comprises a layer of protective coating and the electrically conductive mesh is sandwiched between the electrically insulating substrate and the protective coating.

11. The apparatus according to claim 1 wherein the electrically insulating substrate comprises a polyimide film.

12. The apparatus according to claim 1 wherein the printed electrically conductive mesh has a thickness of from 0.01 to 0.1 mm and/or the electrically insulating substrate has a thickness of from 0.025 to 0.1 mm.

13. The apparatus according to claim 1 wherein the second electrode comprises an electrically conductive knitted wire mesh wrapped around the elongate external surface of the body of dielectric material.

14. The apparatus according to claim 1 wherein the flexible elongate atmospheric plasma generator is circular in transverse cross section.

15. The apparatus according to claim 1 wherein the flexible elongate atmospheric plasma generator has an external diameter of from 1.5 to 5 mm and/or a length of at least 50 cm.

16. The apparatus according to claim 15 wherein the flexible elongate atmospheric plasma generator has an external diameter of from 2 to 5 mm, or from 2 to 3 mm.

17. The apparatus according to claim 15 wherein the flexible elongate atmospheric plasma generator has a length of from 1 to 3 metres, or from 1 to 2 metres.

18. The apparatus according to claim 1 wherein the first electrode is circular in transverse cross section and has an external diameter of from 0.4 to 1 mm, or from 0.5 to 1 mm.

19. The apparatus according to claim 1 wherein the body of dielectric material is composed of a flexible polymer, optionally a silicone elastomeric material, or a flexible ceramic material.

20. The apparatus according to claim 1 wherein the second electrode is coaxially disposed around the first electrode.

21. The apparatus according to claim 1 further comprising an electrical power supply for supplying electrical power to the flexible elongate atmospheric plasma generator to cause the plasma generator to generate a transverse atmospheric plasma, wherein the electrical power supply comprises a control system for controlling the voltage, current and frequency of an alternating current electrical power output, and first and second power terminals respectively connected to the first and second electrodes.

22. The apparatus according to claim 21 wherein the control system is adapted to supply electrical power having a frequency of from 1 to 10 kHz, or 2+/−0.5 kHz, and/or a voltage of from 5 to 15 kVpp, or 9+/−2 kVpp.

23. The apparatus according to claim 21 wherein the control system is adapted to provide electrical power having a current of from 0.5 to 4 mA, or 1.5+/−0.5 mA.

24. An apparatus for sterilising an interior surface of an elongate endoscope tube by an atmospheric plasma, the apparatus comprising a flexible elongate atmospheric plasma generator for generating a transverse atmospheric plasma within, and along a length of, an elongate endoscope tube into which the atmospheric plasma generator has, in use, been inserted, the flexible elongate atmospheric plasma generator being configured for insertion into an end of, and along a length of, an internal channel of an elongate endoscope tube, the flexible elongate atmospheric plasma generator comprising an elongate body of dielectric material, an elongate first electrode centrally located within the body of dielectric material and an elongate second electrode around an elongate external surface of the body of dielectric material, wherein the second electrode comprises a plurality of electrically conductive elements forming a mesh defining holes in the second electrode, wherein the atmospheric plasma generator is configured such that application of a potential difference across the first and second electrodes can generate a plasma within atmospheric air surrounding the atmospheric plasma generator, wherein the atmospheric plasma generator comprises a plurality of elongate modules which are connectable along a length direction to form the elongate atmospheric plasma generator, wherein the elongate modules comprise a first end module comprising a pair of first and second electrical connectors each connected to a respective one of the first and second electrodes, the pair of first and second electrical connectors being located at a first end of the first end module, the first end module having a second end opposite to the first end, a central module having a first end for interlocking electrical connection to the second end of the first end module and an opposite second end, and a second end module comprising a first end for interlocking electrical connection to the second end of the central module and an opposite second end which is electrically insulated.

25. The apparatus according to claim 24 wherein the central module comprises a plurality of sub-modules which are connectable along the length direction to form the central module, wherein each sub-module has a first end and a second end, wherein the first end is for interlocking electrical connection to the second end of the first end module or to a second end of another sub-module and the second end is for interlocking electrical connection to the first end of the second end module or to a first end of another sub-module.

26. The apparatus according to claim 24 wherein each interlocking electrical connection is between a pair of male and female ends of the respective elongate modules, wherein the male end comprises a first transverse layer of electrically insulating material comprising a central projection surrounding the first electrode of the respective module, a transverse first central contact plate electrically connected to the first electrode and disposed on an end surface of the central projection and a transverse first peripheral contact plate electrically connected to the second electrode of the respective module, the first peripheral contact plate being disposed on an end surface of the first transverse layer and located radially outwardly from the first central contact plate, and the female end comprises a second transverse layer of electrically insulating material comprising a central recess surrounding the first electrode of the respective module, a transverse second central contact plate electrically connected to the first electrode and disposed on an inner end surface of the central recess and a transverse second peripheral contact plate electrically connected to the second electrode of the respective module, the second peripheral contact plate being disposed on an end surface of the second transverse layer and located radially outwardly from the second central contact plate, wherein when the pair of male and female ends are in an interlocking electrical connection the first and second central contact plates are urged into electrical contact and the first and second peripheral contact plates are urged into electrical contact.

27. A method of sterilising an interior surface of an elongate endoscope tube by an atmospheric plasma, the method comprising the steps of:
   (a) providing the apparatus according to claim 1;
   (b) inserting the flexible elongate atmospheric plasma generator into an elongate endoscope tube so that the elongate second electrode is in contact with atmospheric air within the elongate endoscope tube; and
   (c) supplying electrical power to the flexible elongate atmospheric plasma generator to cause the plasma generator to generate a transverse atmospheric plasma within the elongate endoscope tube.

28. The method according to claim 27 wherein the electrical power is supplied by a source of alternating current, first and second power terminals respectively connected to the first and second electrodes, and a control system for controlling the voltage, current and frequency of the electrical power, optionally wherein the second electrode is connected to a ground terminal.

29. The method according to claim 27 wherein the electrical power has a frequency of from 1 to 10 kHz, or 2+/−0.5 kHz, and/or a voltage of from 5 to 15 kVpp, or 9+/−2 kVpp.

30. The method according to claim 27 wherein the electrical power has a current of from 0.5 to 4 mA, or 1.5+/−0.5 mA.

31. The method according to claim 27 wherein the transverse atmospheric plasma is generated a within the elongate endoscope tube for a sterilisation treatment period of from 1 to 10 minutes, or from 1 to 5 minutes.

32. The method according to claim 27 wherein the elongate endoscope tube has a length of at least 50 cm, or from 1 to 3 metres, or from 1 to 2 metres, and the flexible elongate atmospheric plasma generator extends along at least 100%, or at least 105%, or at least 110%, of the length of the elongate endoscope tube.

\* \* \* \* \*